(12) United States Patent
Singh et al.

(10) Patent No.: US 10,966,982 B2
(45) Date of Patent: Apr. 6, 2021

(54) STABLE PHARMACEUTICAL FORMULATIONS OF PEMETREXED

(71) Applicant: CIPLA LIMITED, Mumbai (IN)

(72) Inventors: Sarabjit Singh, Navi Mumbai (IN); Alagumurugan Alagarswamy, Thane (IN); Madhusudhan Malladi, Hyderabad (IN); Sandip Gite, Ahmednagar (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 16/689,813

(22) Filed: Nov. 20, 2019

(65) Prior Publication Data

US 2020/0155556 A1    May 21, 2020

(30) Foreign Application Priority Data

Nov. 20, 2018   (IN) .............................. 201821043648

(51) Int. Cl.
   *A61K 31/519*   (2006.01)
   *A61K 39/395*   (2006.01)
   *A61K 33/243*   (2019.01)
   *A61K 47/20*    (2006.01)

(52) U.S. Cl.
   CPC .......... *A61K 31/519* (2013.01); *A61K 33/243* (2019.01); *A61K 39/39558* (2013.01); *A61K 47/20* (2013.01)

(58) Field of Classification Search
   CPC ........................... A61K 31/519; A61K 33/243
   See application file for complete search history.

(56) References Cited

U.S. PATENT DOCUMENTS

| | | | |
|---|---|---|---|
| 6,686,365 B2 | 2/2004 | Riebesehl et al. | |
| 9,265,832 B2 | 2/2016 | Park et al. | |
| 9,421,207 B2* | 8/2016 | Khattar et al. | ....... A61K 31/519 |
| 9,655,898 B2 | 5/2017 | Palepu et al. | |
| 9,968,608 B2 | 5/2018 | Khattar et al. | |

FOREIGN PATENT DOCUMENTS

| | | |
|---|---|---|
| IN | 201821043648 | 11/2018 |
| WO | 2016199053 A1 | 12/2016 |

* cited by examiner

*Primary Examiner* — Kevin E Weddington
(74) *Attorney, Agent, or Firm* — Conley Rose, P.C.; Rodney B. Carroll

(57) ABSTRACT

The present invention relates to a long term storage stable multi-dose ready-to use or ready-to dilute pharmaceutical liquid formulation comprising pemetrexed or a pharmaceutically acceptable salt thereof, an antioxidant, a preservative, a buffering agent, and a pharmaceutically acceptable fluid. The invention also relates to a process of preparing the formulation, a kit and a method of treatment of patients having lung cancer by administering the pharmaceutical formulation to a subject in need thereof.

24 Claims, No Drawings

STABLE PHARMACEUTICAL FORMULATIONS OF PEMETREXED

CROSS-REFERENCE TO RELATED APPLICATIONS

This application claims priority to Indian Application No. 201821043648, filed 20 Nov. 2018 and entitled "STABLE PHARMACEUTICAL FORMULATIONS OF PEMETREXED" which is incorporated herein in its entirety.

BACKGROUND

Pemetrexed belongs to the class of chemotherapy drugs called folate antimetabolites and is used in the treatment of malignant pleural mesothelioma and non-small cell lung cancer. Pemetrexed is the active ingredient in the product available as ALIMTA® Injection by Lilly USA, as a sterile, white to light-yellow or green-yellow sterile lyophilized powder in single-dose vials for reconstitution. Each 100 mg or 500 mg vial of ALIMTA® contains lyophilized pemetrexed disodium equivalent to 100 mg pemetrexed and 106 mg mannitol or 500 mg pemetrexed and 500 mg mannitol respectively, hydrochloric acid and/or sodium hydroxide may have been added to adjust pH.

ALIMTA® product requires reconstitution prior to intravenous infusion. The required dose prior to administration of the product to a patient in need thereof is calculated based on the patient's body surface area (BSA). In order to obtain the required dose, healthcare professionals need to reconstitute 2 or more vials to come up with one dose. The process of reconstitution requires several lengthy and complex steps comprising aseptically reconstituting each vial with 0.9% Sodium Chloride Injection, USP (preservative-free) followed by gently swirling each vial until the powder is completely dissolved so that the resulting solution is clear and ranges in color from colorless to yellow or green-yellow. In addition to this, the resulting solution is further diluted prior to administration.

One of the difficulties with the commercially available formulation of pemetrexed is that the administration process is complex and involves many steps. The procedure involves cumbersome reconstitution steps which add significant time in dose preparation and also presents cytotoxic safety issues for healthcare professionals administering the drug to patients. Although a single dose vial (100 mg and 500 mg) comprising pemetrexed lyophilized formulation is commercially available, the prescribing information states that any unused portion of drug has to be discarded as the formulation does not contain any preservative. Thus, such single dose lyophilized formulation is associated with certain concerns and limitations, such as, the aseptic reconstitution of dry powder is cumbersome and time consuming, there is a potential for dosing errors, exposure of the healthcare professional to cytotoxic vapors and wastage of remaining drug in vial after dose administration of the reconstituted medication. Furthermore, the lyophilization process is also time consuming and often incurs significant expense.

Notably, the reconstituted product and reconstituted-diluted product have limited stability as they have to be stored for no longer than 24 hours under refrigerated conditions and to be discarded after 24 hours from the time of reconstitution. The aqueous solution formulation of pemetrexed powder, when stored at room temperature for a longer period of time, unknown impurities may be formed. The relatively rapid formation of degradants is generally accepted as one of the factors which has prevented aqueous pemetrexed formulations having long-term stability from being commercially available.

U.S. Pat. No. 6,686,365 relates to a liquid formulation of pemetrexed, which comprises a therapeutically effective amount of pemetrexed, an effective amount of an antioxidant and a pharmaceutically acceptable excipient, wherein the antioxidant is selected from the group consisting of monothioglycerol, L-cysteine and thioglycolic acid. However, the drawback of the formulation disclosed in the above patent is, it was reported that, when the formulation was stored at 25° C. for a long period of time, precipitation occurred, suggesting that the long-term stability of the formulation for a desired period cannot be guaranteed.

U.S. Pat. No. 9,265,832 relates to pemetrexed formulation comprising pemetrexed or a pharmaceutically acceptable salt thereof as an active ingredient; N-acetyl-L-cysteine; and a citrate salt.

U.S. Pat. No. 9,968,608 is directed towards pharmaceutical composition comprising pemetrexed tromethamine, and water or an organic solvent, wherein the tromethamine is present in 40% to 90% by weight of the pemetrexed and the pharmaceutical composition is a liquid by virtue of inclusion of the water or the organic solvent.

U.S. Pat. No. 9,655,898 is directed towards long term storage stable pemetrexed-containing aqueous liquid pharmaceutical composition, comprising pemetrexed or a pharmaceutically acceptable salt thereof, 1 mg/ml to about 20 mg/ml L-methionine, and 0.005M to about 0.5M sodium citratetribasic, and an aqueous pharmaceutically acceptable fluid, and preferably propylene glycol, wherein the composition has a pH of from about 8.0 to about 9.5.

WO 2016199053 describes a ready-to-use liquid parenteral pharmaceutical formulation of pemetrexed comprising pemetrexed diacid, one or more amino acids, one or more solvents, and optionally other pharmaceutically acceptable adjuvants.

However, all attempts made in the past only provide either short term storage products, single dose formulations, or ready to use formulations. Thus, there exists a need for simple and cost-effective methods of formulating stable ready-to-use or ready-to-dilute multi-dose pemetrexed formulations having high and long term storage stability.

As pemetrexed formulation has limited stability and in view of degradation products formed during the storage, development of long term storage stable multi-dose pemetrexed dosage form such as an ready to dilute or ready to use injection is very challenging. Furthermore, the chances of microbial contamination occurring when such products are stored for long time are also high.

The present invention addresses the need for a pharmaceutically stable multi-dose pemetrexed formulation having long term storage stability and having regard to retaining the solution dosage form and avoiding unacceptable degradation of substances in the formulation.

SUMMARY OF THE INVENTION

The present invention provides a pharmaceutical formulation comprising: a) pemetrexed or a pharmaceutically acceptable salt thereof; b) an antioxidant; c) a preservative; d) a buffering agent; and e) a pharmaceutically acceptable fluid. Preferably, the pharmaceutical formulation is a long term storage stable multi-dose ready-to-dilute or a ready-to-use pemetrexed liquid formulation. The ready-to-dilute or a ready-to-use pemetrexed formulation may be a solution or a concentrate. The pharmaceutical formulation when stored for six months in a sealed, sterile vial at 25° C./60% RH and 40° C./75% RH contains no more than 1.0% total impurity as measured by HPLC. The present invention also provides a process of preparing a pharmaceutical formulation comprising: a) pemetrexed or a pharmaceutically acceptable salt thereof; b) an antioxidant; c) a preservative; d) a buffering agent; and e) a pharmaceutically acceptable fluid, which may be a long term storage stable multi-dose ready-to-dilute or ready to use pemetrexed formulation.

The present invention also provides a method for treating patients suffering from locally advanced or metastatic, non-squamous, non-small cell lung cancer by administering ready-to-dilute or ready-to-use parenteral formulations of pemetrexed, either alone or in combination with a suitable anticancer agent. Preferably, the anticancer agent is cisplatin, carboplatin, pembrolizumab or combinations thereof.

The inventors have found that a pharmaceutical formulation comprising: a) pemetrexed or a pharmaceutically acceptable salt thereof; b) an antioxidant; c) a preservative; d) a buffering agent; and e) a pharmaceutically acceptable fluid, does not require a cumbersome procedure of dry powder reconstitution, it is easy to administer, lead to reduced exposure to drug's cytotoxic vapors during reconstitution by healthcare providers, and also demonstrate reduction in dosing errors. Preferably, the pharmaceutical formulation disclosed herein is in the form of a multi-dose vial, which provides greater flexibility at the pharmacy and clinics for healthcare providers to prepare different dose combinations for multiple patients.

The present inventors have also found that a combination of an antioxidant, a preservative and a buffering agent along with pemetexed or its derivatives provides a multi-dose and long term storage stable product, which is suitable for parenteral administration. The present inventors have also found that the pharmaceutical pemetrexed formulation disclosed herein is safe, efficacious, easy to use and has a high strength of pemetrexed which obviate multiple vial reconstitution for larger doses.

DETAILED DESCRIPTION OF THE INVENTION

The drug compound "pemetrexed" has a chemical name N-[4-[2-(2-amino-4,7-dihydro-4-oxo-1H395 pyrrolo[2,3-d]pyrimidin-5-yl)ethyl]benzoyl]-L-Glutamic acid and is active as disodium salt, heptahydrate. Its structural formula is shown below.

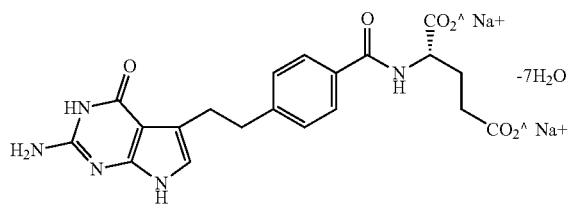

Pemetrexed has the molecular formula of $C_{20}H_{19}N_5Na_2O_6 \cdot 7H_2O$ and has molecular weight of 597.49. Pemetrexed is a white to off-white powder. It is practically insoluble in water and very slightly soluble under acidic conditions.

Pemetrexed is a folate analog metabolic inhibitor that disrupts folate-dependent metabolic processes essential for cell replication. In vitro studies have shown that pemetrexed inhibits thymidylate synthase (TS), dihydrofolate reductase, and glycinamide ribonucleotide formyltransferase (GARFT), which are folate-dependent enzymes involved in the de novo biosynthesis of thymidine and purine nucleotides. Pemetrexed is taken into cells by membrane carriers such as the reduced folate carrier and membrane folate binding protein transport systems. Once in the cell, pemetrexed is converted to polyglutamate forms by the enzyme folylpolyglutamate synthetase. The polyglutamate forms are retained in cells and are inhibitors of TS and GARFT.

The term "pemetrexed" is used in a broad sense to include not only "pemetrexed" per se, but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

The present invention provides stable multi-dose pharmaceutical formulations comprising pemetrexed or its pharmaceutically acceptable salts, isomers, racemates, enantiomers, hydrates, solvates, metabolites, polymorphs, and mixtures thereof. Preferably, pemetrexed is the disodium salt thereof.

In one embodiment, the pharmaceutical formulation described herein is free of amino acid.

In some embodiments, the pharmaceutical formulations are in the form of ready-to-dilute and/or ready-to-use solutions or concentrates. The ready-to-dilute and ready-to-use formulations may be packaged within a conventional sterile vial or other container. Alternatively, the formulations may be packaged in a sterile syringe already fitted with a needle for injection.

In some embodiments, the pharmaceutical formulations are stable injectable formulations of pemetrexed ready for direct dilution with an infusion solution, without any need for preparation of premix solutions, and manufacturing processes thereof.

In some embodiments, the pharmaceutical formulations are multi-dose vial formulations of pemetrexed, ready for direct dilution with infusion solution.

In another embodiment, the pharmaceutical formulations are multi-dose vial formulations of pemetrexed, ready for direct introduction into an infusion bag or direct dilution with an infusion solution.

In some embodiments, the pharmaceutical formulations are stable ready-to-use formulations of pemetrexed for direct administration without further dilutions.

The term "composition" or "formulation" or "dosage form" has been employed interchangeably for purposes of the present invention and refers to a pharmaceutical composition which is suitable for administration to a patient or subject. The subject can be an animal, preferably a mammal, more preferably a human.

The term "administration" or "administering," as used herein, refers to a method of giving a dosage of a compound or composition to subject, such as an animal, preferably a mammal, more preferably a human via a suitable mode of administration. In various embodiments as will be disclosed herein, the preferred mode of administration can be parenteral administration, injectable formulations administered via any route including intramuscular, intravenous, or subcutaneous.

The term "stable formulations" refers that pemetrexed formulations of present invention are physically as well as chemically stable as demonstrated by compliance to acceptable specification when the formulation is stored at convenient temperature, such as between about 0° C. and about 60° C., for a commercially reasonable period of time, such as at least about 1 day, at least about 1 week, at least about 1 month, at least about 3 months, at least about 6 months, at least about 1 year, or at least about 2 years.

For purposes of the present invention, "long term storage" shall be understood to include at least time periods which are in excess of those observed when currently available lyophilized pemetrexed formulations are reconstituted.

In various embodiments as disclosed herein, the solution of pemetrexed formulation of present invention remains physically stable, with no precipitation or crystallization or color change upon storage and the value of percentage transmittance of the solution remaining greater than 90%, preferably greater than 95% for the shelf life period of 18-24 months when stored at room temperature. Suitably, the solution of pemetrexed formulation of present invention remains chemically stable when stored at room temperature (about 25° C.) and at refrigerated conditions (2-8° C.), wherein various parameters such as the drug content (assay of pemetrexed) and content of related substances, i.e. known and unknown impurities remains within specified limits such as those specified according to ICH guidelines, upon storage for prolonged period of time such as for at least 6 months, at least 12 months, preferably for 18 months, more preferably 24 months or longer. The formulations of present invention are substantially free of impurities. For purposes of the present invention, "substantially free of impurities' shall be understood to include pemetrexed containing formulations in which the amount of total impurities is less than about 5% of the sum of peak areas of all degradants, as calculated on a normalized peak area response ("PAR) basis as determined by high performance liquid chromatograph ("HPLC) after a period of about 6 months at a temperature of from about 5° C. to about 25° C. The amount of impurities is further calculated as being based upon the original amount of pemetrexed (or salt thereof) being present in the composition or formulation. Preferably, the stable formulations of pemetrexed of the present invention prevent degradation of pemetrexed such that not more than 2%, not more than 1%, not more than 0.4%, not more than 0.2% of pemetrexed impurity or impurities are formed over the storage period.

Preferably, the value of assay of pemetrexed formulation of the present invention remains within the specified limit of 90-110% by weight of the label claim; the highest unknown impurity remains within the specified limit of not more than 0.2%; the known impurities A (Relative Retention Time (RRT) about 0.82), B (Relative Retention Time (RRT) about 0.86), C (Relative Retention Time (RRT) about 0.87), and D (Relative Retention Time (RRT) about 0.90), remain within the specified limit of not more than 0.29% and the impurity A remains within the specified limit of not more than 1.0%. The total impurities in the formulation remain below 2.0%, preferably below 1.0%.

In some embodiments, the time period for which long term storage is contemplated includes periods of at least about 6 months or longer such that the formulation is substantially free of impurities when stored at a room temperature.

The term "multi-dose formulation" refers to formulations that are contained in vials (multi-dose containers) that allow for the extraction of partial amounts of the formulation at various times and are stored at refrigeration temperature or room temperature for long period of time. In various embodiments as disclosed herein, the pemetrexed formulations of the present invention allow multiple doses to be obtained from a single container, and allows for more controlled administration of the pharmaceutical composition/formulation as the formulation may be withdrawn and administered to a patient in need thereof in any partial amount.

The term 'ready-to-dilute' used herein refers to aqueous preconcentrates, solutions which require a single step of dilution with an aqueous diluent fluid such as water for injection or saline before administration. The term "ready-to-dilute" is distinguished from lyophilized products that require two steps, a first step of reconstitution to form a preconcentrate and then a second step where the preconcentrate is subjected to dilution with an aqueous infusion fluid. In some embodiments, the ready-to-dilute formulation may be provided as a single vial containing the pemetrexed formulation. In other embodiments, the ready-to-dilute formulation may be accompanied by a pharmaceutically acceptable diluent in a separate container (i.e., a dual vial formulation).

The ready-to-dilute formulation according to the present invention is a parenteral formulation. The ready-to-dilute parenteral formulation of the present invention avoids the inconvenience of reconstituting a concentrated parenteral formulation into infusion diluents prior to infusion, as well as eliminates the risk of any potential calculation or dilution error as well as risk of microbiological contamination during handling.

Preferably, the ready-to-dilute parenteral formulation dosage form is a prefilled syringe or an infusion bag comprising the formulation. In some embodiments, the volume of the aqueous drug solution is large based on the end use dosage form. In an example, the volume of the aqueous solution in 'ready-to-dilute' parenteral dosage form which is a prefilled syringe may be about 50 ml to 100 ml. When the dosage form is an infusion bag, the volume of the aqueous solution may be about 100 ml to 500 ml.

The term "ready-to-use" refers to any preparation of pemetrexed which can be administered to patient directly without any further dilution or processing. In another embodiment, the formulation of present invention is 'ready-to-use' formulation which does not require dilution before administration.

In some embodiments, the pharmaceutical formulation, preferably in the form of a parenteral formulation, comprises pemetrexed or pharmaceutically acceptable salts thereof at concentrations from about 1 mg/mL to about 100 mg/mL. In some embodiments, the concentrations of pemetrexed or pharmaceutically acceptable salts thereof in the formulations are in the range from about 10 mg/mL to about 50 mg/mL, or about 10 mg/mL to about 30 mg/mL, preferably 25 mg/mL in ready-to-dilute formulation, and preferably 5 mg/mL in ready-to-use formulation.

In some embodiments, the pharmaceutical formulations are preferably in the form of an injectable formulation. Injectable formulations disclosed herein can be formulated as aqueous solutions. Injectable formulations can be prepared in conventional forms, either as liquid or solutions ready for dilution or ready to use Sterile injectable formulations can be prepared according to techniques known in the art using suitable carriers, excipients, dispersing or wetting agents, and suspending agents. The injectable formulations may be sterile injectable solutions in a nontoxic, parenterally acceptable diluent or solvent. Among the acceptable vehicles and diluents or solvents that may be employed include, but not limited to water for injection, isotonic dextrose solution, isotonic sodium chloride solution, and the like, useful and safe for parenteral administration. In some embodiments, the pharmaceutical formulations are ready-to-use formulations, in which the isotonicity agent is 0.9% NaCl solution.

In some embodiments, the pharmaceutical formulations of the present application are particularly suited for use in parenteral administration, but it will be understood that the solutions may have alternative uses. Injectable formulations may be administered via any route including intramuscular, intravenous, or subcutaneous.

In some embodiments, the pharmaceutical formulations of the present application may be in the form of liquid concentrates, ready-to-dilute and/or ready-to-use solutions.

In some embodiments, the pharmaceutical formulations of the present application further comprise antioxidant. Suitable antioxidants include but not limited to, monothioglycerol, L-cysteine and thioglycolic acid, acetyl cysteine, butylated hydroxy toluene, butylated hydroxy anisole, DL-tocopherol, sodium metabisulfite, sodium formaldehyde sulfoxylate, EDTA and its derivatives, methionine, ascorbic acid, citric acid and its pharmaceutically acceptable salt, sodium sulfite and its derivative and the like. Preferably, the antioxidant concentration in the formulation of the present invention is in the range of about 1 mg/mL to about 25 mg/mL, or the saturation solubility, whichever is higher in the final formulation. Preferably, the antioxidant concentration in the formulation is in the range of about 2 mg/mL to about 10 mg/mL, and more preferably the antioxidant concentration is in the range of about 2.5 mg/mL to about 5 mg/mL. In some preferred embodiment, the antioxidant is monothioglycerol. Preferably, monothioglycerol is present at a concentration range of about 2 mg/mL to 10 mg/mL of the formulation.

Without meaning to be bound by any theory or hypothesis, metal ion induced oxidation of pemetrexed is caused by metal ions leached from the surface of the glass containers or from the elastomeric composition of the stopper in which pemetrexed formulations were stored. The presence of an antioxidant stabilizes pemetrexed solution during long term storage.

In some embodiments, the formulations of the present application further comprise preservatives, preferably antibacterial preservatives. To ensure that multi-dose formulations maintain optimally sterile properties, the United States Food and Drug Administration (FDA) and regulatory agencies in other jurisdictions require that all multi-dose formulations contain preservatives to prevent the growth of, or to affirmatively kill, any microorganisms that may be introduced into the formulations. Suitable preservatives include but not limited to, one or more of phenylmercuric nitrate, thiomersal, benzalkonium chloride, benzethonium chloride, phenol, cresol and chlorobutanol and the combination thereof. In a preferred embodiment, the preservative is selected from the group comprising benzyl alcohol, parabens, phenol and mixtures thereof. Benzyl alcohol, which has the dual ability to preserve the solution and to act as a local anesthetic to alleviate injection site discomfort is preferred. The concentration of the preservatives in the formulation may be range from about 0.05 mg/mL to about 30 mg/mL, and preferably in the range of about 0.1 mg/mL to about 25 mg/mL. In most preferred embodiment, the preservative is benzyl alcohol. Preferably, benzyl alcohol is present in the formulation of the present invention at a concentration range of about 3 mg/mL to 25 mg/mL of the formulation. In another preferred embodiment, the preservative is m-cresol. Preferably, m-cresol is in the formulation of the present invention at a concentration range of 0.1 mg/mL to 3 mg/mL of the formulation. In another preferred embodiment, the preservative is m-cresol, benzyl alcohol or combination thereof.

In some embodiments, the formulations of the present application further comprise buffering agents. Buffering agents are useful in the present invention for, among other purposes, manipulation of the total pH of the pharmaceutical formulation. Suitable include but not limited to, various salts of organic or inorganic acids, including hydrochloric acid, bases, or amino acids, various forms of citrate, phosphate, tartrate, succinate, adipate, maleate, lactate, acetate, bicarbonate, or carbonate ions, sodium hydrochloride or combinations thereof. The concentration of the buffering agent in the formulation may be in the range of about 0.5 mg/mL to about 30 mg/mL or may be in the range of about 1 mg/mL to about 20 mg/mL. In a preferred embodiment, the buffering agent is sodium citrate tribasic. Preferably, the concentration of sodium citrate is in the range of about 1 mg/mL to about 20 mg/mL The pH of the formulation can be changed based on the amount of buffering agent used. In some embodiments, the formulation is prepared such that the preferred pH level of the formulation is from about 5.0 to about 9.0, more preferred is a pH from about 8.0.

In some embodiments, the formulations of the present application further comprise a pharmaceutically acceptable fluid. Suitable pharmaceutically acceptable fluid include but not limited to, aqueous solutions, water, saline, $D_5W$, or mixtures thereof. In several embodiments of the invention, the pharmaceutical formulations include water as a pharmaceutically acceptable fluid. In other embodiments of the invention, however, the pharmaceutical formulations include a mixture of propylene glycol (PG) and water. For example, in one embodiment, the pharmaceutical formulations of the present invention include about 10% propylene glycol and about 90% water. Alternatively, the pharmaceutical formulations can include about 25% propylene glycol and about 75% water. In other embodiments, the pharmaceutical formulations can include up to about 75% propylene glycol. The amount of water and propylene glycol can be varied within the ranges, i.e. the ratio of water to propylene glycol in the pharmaceutical compositions can range from about 100% to 0% to about 25% to up to about 75%. Within this range, are pharmaceutical formulations including up to about 75% propylene glycol and greater than about 25% water, and pharmaceutical formulations including about 50% water and 50% propylene glycol.

The formulation of present invention exhibits acceptable stability, retains a pharmaceutically desirable appearance, maintains the desired enantiomeric stability. Further, the formulation provided herein, is suitable for parenteral dosage.

While not wishing to be bound by any theory whatsoever, it is believed that the use of anhydrous excipients such as, buffers, antioxidants, surfactants, preservatives and isotonicity agents in preparing pemetrexed formulations of the present invention may play a significant role in reducing the degradation of pemetrexed thereby prolonging the shelf-life of pemetrexed formulations.

In a preferred embodiment of the present invention, the long term storage stable multi-dose pharmaceutical formulation comprises: a) pemetrexed; b) monothioglycerol, disodium EDTA or mixture; c) sodium citrate tribasic; d) benzyl alcohol and d) a pharmaceutically acceptable fluid e) NaOH/HCl; and preferably the formulation has a pH of about 7.5 or 8.

In a preferred embodiment of the present invention, the long term storage stable multi-dose pharmaceutical formulation comprises: a) pemetrexed; b) monothioglycerol, disodium EDTA or mixture; c) sodium citrate tribasic; d) m-cresol and e) propylene glycol and water; f) NaOH/HCl, and preferably the formulation has a pH of about 7 or 8.

In some embodiments, the pharmaceutical formulation is in the form of a multi-dose injection concentrates. The multi-dose injection concentrates can be prepared by methods known in the art. For example, one or more of the ingredients (pemetrexed or its derivatives and excipients such as buffers, antioxidants, surfactants, preservatives, pharmaceutically acceptable fluid and isotonicity agents) may be added to each other and then placed into a common receptacle for mixing, or the ingredients may be added to a common receptacle in a particular order, or the ingredients may be added to a common receptacle simultaneously.

The ingredients of the multi-dose injection may be mixed by methods known in the art. For example, the ingredients can be mixed by simple mixing, or may be mixed with a mixing device continuously, periodically, or a combination thereof. Mixing devices may include, but are not limited to, a magnetic stirrer, shaker, a paddle mixer, homogenizer, and any combination thereof.

The addition and mixing of one or more ingredients of the multi-dose injection may occur under controlled conditions. For example, the addition and mixing of the ingredients may occur under conditions such as under nitrogen or at a particular humidity, etc., or the adding and mixing may occur under certain temperatures. In certain embodiments, the adding and mixing may occur under temperature conditions of about 25° C. to about 80° C.

Furthermore, the addition and mixing may be under controlled light exposure, such as in yellow light or under protection from direct exposure to light. After the injection concentrate is prepared, it may be sterilized by methods known in the art. The injection concentrate may undergo aseptic filtration (e.g., using a 0.2 µm disposable pre-sterilized membrane filter). Additionally, the injection concentrate may be placed into a container (e.g., an intravenous solution bag, bottle, vial, ampoule, or pre-filled sterile syringe). The container may have a sterile access port for piercing by a hypodermic injection needle. In some embodiments, the injection concentrate may be filled in one or more pre-sterilized depyrogeneated vials and stopped aseptically with a pre-sterilized butyl stopper. In some embodiments, the injection concentrate may be filled in sterile syringe.

The diluted injection concentrate may be formed by mixing the injection concentrate and diluent together. In one embodiment the injection concentrate may be added to the diluent. In another embodiment, the diluent may be added to the injection concentrate. In yet another embodiment, the multi-dose injection concentrate and diluent may be combined together in a pre-sterilized vessel. The multi-dose injection concentrate and diluent may be mixed by repeated inversions, swirling, or other techniques known in the art.

The final dilution for infusion may be prepared by combining the injection concentrate or a diluted injection concentrate with an infusion solution comprising the formulation of the present invention, according to methods known in the art. For example, the concentrate or a diluted injection concentrate may be mixed with an infusion solution in a common receptacle, or the injection concentrate or the diluted injection concentrate may be injected into an infusion bag containing the infusion solution.

Another embodiment of present invention is directed to delivery of pemetrexed, once diluted to appropriate injection (especially infusion, most particularly IV infusion) concentrations, it may be administered in appropriate amounts for treating pemetrexed responsive conditions known in the art.

The present invention also provides a method of preparing pemetrexed-containing formulation described herein. The method comprises dissolving pemetrexed or pharmaceutically acceptable salt thereof in a pharmaceutically acceptable fluid. to form a solution; adding an antioxidant; a preservative; and a buffering agent to the solution; and adjusting the pH of the solution to from about 5.0 to about 8. The obtained sterile solution may then be filled in vials, sealed, labelled and preferably maintained at 40° C. and 25° C.

The present invention also provides a method of preventing the formation of pemetrexed degradants in liquid pemetrexed-containing formulations during long term storage at room temperature. The method includes dissolving a sufficient amount of pemetrexed or a pharmaceutically-acceptable salt thereof in a pharmaceutically acceptable fluid to form a solution and adding an antioxidant, a preservative; and a buffering agent to the solution and adjusting the pH to from about 5 about 8. The preferred antioxidants, preservatives and buffering agents are as described in the pharmaceutical formulations of the present invention. The obtained sterile solution is then filled in vials, sealed, labelled and preferably maintained at 40° C. and 25° C. In some embodiments, the liquid pemetrexed-containing formulation is prepared such that the preferred pH level of the formulation is between about 6.0 to about 8.0, and most preferable is to develop a formulation having a pH of about 8.0.

The present invention also provides a kit and/or pharmaceutical container for holding the pemetrexed-containing formulation described herein. The kit may contain at least one pharmaceutically acceptable vial or container containing one or more doses of the pemetrexed-containing formulations of the present invention as well as other pharmaceutically necessary materials for storing and/or administering the drug, including instructions for storage and use, infusion bag or container with normal saline or $D_5W$, additional diluents, if desired, etc. The diluent may also optionally include any known fluids capable of being included in sterile parenteral formulations. Such aqueous-based suitable fluids can include, for example, saline or dextrose if desired as well any of the known ancillary preservatives or excipients commonly found as part of parenteral formulations. In accordance with current FDA requirements, vials containing the formulations described herein contain well below the acceptable limits for particulate matter. In some embodiments, the vials contain:

Particles=10 µm: Not more than 6000 per container (average)

Particles=25 µm: Not more than 600 per container (average).

The formulations/compositions of the present invention can be packaged in any suitable sterile vial or container fit for the sterile storage of a pharmaceutical such as pemetrexed for extended periods of time. Suitable containers can be glass vials, i.e. Schott treated vials, molded glass vials, and CZ resin vials, polypropylene or polyethylene vials or other special purpose containers. Containers are of a size sufficient to hold one or more doses of pemetrexed.

The present invention also provides a method for treating patients suffering from malignant pleural mesothelioma or locally advanced or metastatic, non-squamous, non-small cell lung cancer by administering a formulation of pemetrexed as described herein either alone or in combination with an anti-cancer drug. Preferably, the formulation is administered to a patient in need thereof, in combination with cisplatin or carboplatin plus pembrolizumab. The present invention also provides a method for treating patients with locally advanced or metastatic, non-squamous, non-small cell lung cancer by administering a stable ready-to-dilute or ready-to-use parenteral formulation of pemetrexed described herein either alone or in combination with in combination with cisplatin or carboplatin plus pembrolizumab.

The following examples are for the purpose of illustration of the invention only and are not intended to limit the scope of the present invention in any manner whatsoever.

Parenteral compositions of Pemetrexed were prepared by using the following methodology:

Example 1: Composition of the Formulation of Pemetrexed Disodium RTD Injection

| Ingredients | Quantity (mg/ml) |
| --- | --- |
| Pemetrexed | 25 |
| Monothioglycerol | 5 |
| Sodium Citrate tribasic | 14.7 |
| M-cresol | 3 |
| NaOH/HCl | q.s to adjust pH to 6 to 9.5 |
| Water for injection | q.s to adjust to 1 mL |
| Nitrogen | Q.S. to achieve the oxygen level below 3 ppm |

Procedure:

Pemetrexed-containing compositions were prepared by dissolving pemetrexed disodium salt to a concentration of 25 mg/ml in water. Monothioglycerol, sodium citrate tribasic and M-cresol was added to solution. The pH was adjusted to 6 to 9.5 with 0.1N sodium hydroxide or 0.1 N hydrochloric acid. The obtained sterile solution is then filled in vials, sealed, labelled and were maintained at 40° C. and 25° C. and analyzed for preservative test.

Preservative Efficacy Test:

Preservative effectiveness tests are compendial-guided assays that determine efficacy for preservative systems in pharmaceutical preparations. In such assays, test formulations are challenged with standardized suspensions of indicator aerobic bacteria and molds and microorganism survival is monitored over a 28-day period. The efficacy of the preservative against various microorganisms was measured using a USP/EP preservative efficacy test. These tests were conducted on Memmert equipment. In the procedure, formulations were tested against the following microorganisms:

*Escherichia coli, Staphylococcus aureus, Pseudomonas aeruginosa, Candida albicans*, and *Aspergillus niger.*

The bacterial strains and fungi were inoculated at a total concentration of ~10 cfu/mL. Samples were incubated for 7 days at room temperature (25° C.), and the total bacterial and fungal counts were measured using a colony counter. The log reduction (LR) values for the bacterial and fungal counts were calculated as log (initial count/final count).

| | | | Log reduction | | | |
| --- | --- | --- | --- | --- | --- | --- |
| S. No | Organism used | Initial | $7^{th}$ day | $14^{th}$ day | $28^{th}$ day | Remark |
| 1. | *Escherichia coli* | 1.3391 | 5.1173 | 5.1173 | 5.1173 | Complies |
| 2. | *Pseudomonas aeruginosa* | 5.9956 | 5.9956 | 5.9956 | 5.9956 | Complies |
| 3. | *Staphylococcus aureus* | 0.2253 | 5.2253 | 5.2253 | 5.2253 | Complies |
| 4. | *Candida albicans* | 0.0384 | 5.3729 | 5.3729 | 5.3729 | Complies |
| 5. | *Aspergillus Brasiliensis* | −0.097 | 5.5051 | 5.5051 | 5.5051 | Complies |

Observation:

The aqueous formulation comprising monothioglycrol as antioxidant, m-cresol as preservative and a buffering agent pass the preservative efficacy test.

Example 2: Composition of the Formulation of Pemetrexed Disodium RTD Injection

| Ingredients | Quantity (mg/ml) |
| --- | --- |
| Pemetrexed | 25 |
| Monothioglycerol | 4 |
| Sodium Citrate tribasic | 14.7 |
| Benzyl Alcohol | 7.5 |
| NaOH/HCl | q.s to adjust pH to 6 to 9.5 |
| Water for injection | q.s to adjust to 1 mL |
| Nitrogen | Q.S. to achieve the oxygen level below 3 ppm |

Procedure:

Pemetrexed-containing compositions were prepared by dissolving pemetrexed disodium salt to a concentration of 25 mg/ml in water. Monothioglycerol, sodium citrate tribasic and Benzyl Alcohol was added to solution. The pH was adjusted to 6 to 9.5 with 0.1N sodium hydroxide 0.1 N hydrochloric acid. The samples were maintained at 40° C. and 25° C. and analysed for drug content and impurity profile.

Stability Testing:

| | Related substances (%) | | | | | | |
|---|---|---|---|---|---|---|---|
| Parameter | Imp A (RRT 0.82) | Imp B (RRT 0.86) | Imp C (RRT 0.87) | Imp D (RRT 0.90) | RRT 0.621 | Any Unspecified Impurity | Total impurities |
| Initial | 0.01 | 0.03 | 0.04 | 0.09 | 0.07 | 0.07 (RRT 0.62) | 0.26 |
| 25° C. ± 2° C./60% ± 5% RH | | | | | | | |
| 1 M | 0.02 | 0.02 | 0.04 | 0.1 | 0.09 | 0.09 (RRT 0.62) | 0.33 |
| 3 M | <0.05 | <0.05 | <0.05 | <0.05 | <0.05 | 0.29 (RRT 1.35) | 0.29 |
| 6 M | <0.05 | <0.05 | <0.05 | <0.05 | <0.05 | 0.46 (RRT 1.35) | 0.46 |
| 40° C. ± 2° C./75% ± 5% RH | | | | | | | |
| 1 M | 0.01 | 0.03 | 0.04 | 0.09 | <0.05 | 0.15 (RRT 1.332) | 0.47 |
| 3 M | <0.05 | <0.05 | <0.05 | <0.05 | <0.05 | 0.51 (RRT 1.35) | 0.51 |
| 6 M | <0.05 | <0.05 | <0.05 | <0.05 | <0.05 | 0.75 (RRT 1.35) | 0.75 |

Preservative Efficacy Test:
The procedure followed was same as example 1.

| | | | Log reduction | | | |
|---|---|---|---|---|---|---|
| S. No | Organism used | Initial | 7$^{th}$ day | 14$^{th}$ day | 28$^{th}$ day | Remark |
| 1. | *Escherichia coli* | 0.0418 | 5.1173 | 5.1173 | 5.1173 | Complies |
| 2. | *Pseudomonas aeruginosa* | 0.2713 | 5.9956 | 5.9956 | 5.9956 | Complies |
| 3. | *Staphylococcus aureus* | −0.1726 | 5.2253 | 5.2253 | 5.2253 | Complies |
| 4. | *Candida albicans* | −0.0109 | 5.3729 | 5.3729 | 5.3729 | Complies |
| 5. | *Aspergillus Brasiliensis* | 0.2041 | 5.5051 | 5.5051 | 5.5051 | Complies |

Observation:

The pemetrexed injection is very stable in solutions containing an monothioglycerol as an antioxidant and a sodium citrate as a buffering agent and benzyl alcohol for a period of one month at 40° C.±2° C./75%±5% RH. The results of preservative efficacy tests indicate that benzyl alcohol is effective in preserving the formulation against both bacteria and fungi.

Example 3: Comparative Examples for Antimicrobial Effectiveness of Preservatives Various types of formulations were prepared and studies for selection and optimization of preservatives. Some formulations were also prepared preservative free and were compared for the stability and antimicrobial effectiveness test.

Formulation A: Preservative Free Formulation

| Composition | Concentration per vial basis (mg/ml) |
|---|---|
| Pemetrexed | 25 |
| Monothioglycerol | 5 |
| Sodium Citrate tribasic | 14.7 |
| NaOH/HCl | q.s to adjust pH to 6 to 9.5 |
| Water for injection | q.s to adjust to 1 mL |
| Nitrogen | Q.S. to achieve the oxygen level below 3 ppm |

Procedure:

Pemetrexed disodium salt was dissolved in water to a concentration of 25 mg/ml. Monothioglycerol and sodium citrate tribasic was added to the solution. The pH was adjusted to between 6 to 9.5 with 0.1N sodium hydroxide or 0.1 N hydrochloric acid. The obtained sterile solution is then filled in vials, sealed, labelled and were maintained at 40° C. and 25° C. and analysed for drug content, impurity profile and preservative efficacy test.

Formulation B: Formulation with Preservatives

| Ingredients | Quantity (mg/ml) |
|---|---|
| Pemetrexed | 25 |
| Monothioglycerol | 5 |
| Sodium Citrate tribasic | 14.7 |
| Benzyl alcohol | 25 |
| NaOH/HCl | q.s to adjust pH to 6 to 9.5 |
| Water for injection | q.s to adjust to 1 mL |

-continued

| Ingredients | Quantity (mg/ml) |
|---|---|
| Nitrogen | Q.S. to achieve the oxygen level below 3 ppm |

Procedure:

Pemetrexed-containing compositions were prepared by dissolving pemetrexed disodium salt to a concentration of 25 mg/ml in water. Monothioglycerol, sodium citrate tribasic and Benzyl alcohol were added to the solution. The pH was adjusted to 6 to 9.5 with 0.1N sodium hydroxide or 0.1 N hydrochloric acid. The obtained sterile solution is then filled in vials, sealed, labelled and were maintained at 40° C. and 25° C. and analyzed for drug content and impurity profile.

Stability Testing:

| Formulation | Parameter | Imp A (RRT 0.82) | Imp B (RRT 0.86) | Imp C (RRT 0.87) | Imp D (RRT 0.90) | RRT 0.606 | Any Unspecified Impurity | Total impurities |
|---|---|---|---|---|---|---|---|---|
| A | Initial | ND | 0.03 | 0.03 | 0.09 | 0.07 | 0.07 | 0.23 |
| B |  | 0.010 | 0.03 | 0.040 | 0.090 | — | 0.070 | 0.220 |
| 25° C. ± 2° C./60% ± 5% RH | | | | | | | | |
| A | 1 M | 0.008 | 0.038 | 0.045 | 0.113 | 0.177 | 0.177 | 0.51 |
| B |  | 0.01 | 0.03 | 0.03 | 0.09 | 0.08 | 0.09 | 0.31 |
| 40° C. ± 2° C./75% ± 5% RH | | | | | | | | |
| A | 1 M | 0.039 | 0.039 | 0.045 | 0.117 | 0.172 | 0.172 | 0.72 |
| B |  | 0.010 | 0.040 | 0.090 | 0.110 | 0.35 | 0.35 | 0.710 |

Preservative Efficacy Test:

The procedure followed was same as example 1.

| S. No | Organism | Formulation | Initial | 7th day | 14th day | 28th day | Remark |
|---|---|---|---|---|---|---|---|
| 1. | Escherichia coli | A | 0.0054 | −1.0360 | −0.6936 | −0.4717 | Does not comply |
|  |  | B | 5.9085 | 5.9085 | 5.9085 | 5.9085 | Complies |
| 2. | Pseudomonas aeruginosa | A | 0.0103 | −0.9157 | −1.0200 | −0.5757 | Does not comply |
|  |  | B | 0.9899 | 5.9294 | 5.9294 | 5.9294 | Complies |
| 3. | Staphylococcus aureus | A | 0.0139 | −0.9199 | −0.4537 | −0.1776 | Does not comply |
|  |  | B | 2.0382 | 5.9777 | 5.9777 | 5.9777 | Complies |
| 4. | Candida albicans | A | 0.0235 | 0.1404 | 3.0955 | 3.2373 | Complies |
|  |  | B | 1.1099 | 5.8808 | 5.8808 | 5.8808 | Complies |
| 5. | Aspergillus Brasiliensis | A | 0.0322 | 0.1408 | 0.1684 | 0.2168 | Complies |
|  |  | B | 1.067 | 5.4472 | 5.4472 | 5.4472 | Complies |

(Log reduction columns: Initial, 7th day, 14th day, 28th day)

Observation:

The aqueous formulations A and B of pemetrexed are both stable for a period of one month at 25° C.±2° C./60%±5% RH and 40° C.±2° C./75%±5% RH. However, formulation A (preservative free) fails the preservative efficacy test and thus is not suitable for long term storage. Formulation B (with preservative) pass the preservative efficacy test.

Example 4: Composition of the Formulation of Pemetrexed Disodium RTU Injection

| Composition | Concentration per vial basis (mg/ml) |
| --- | --- |
| Pemetrexed | 10 |
| Monothioglycerol | 1.4 |
| Sodium Citrate tribasic | 5.88 |
| Sodium Chloride | 2 |
| Benzyl Alcohol | 3 |
| NaOH/HCl | q.s to adjust pH to 6 to 9.5 |
| Water for injection | q.s to adjust to 1 mL |
| Nitrogen | Q.S. to achieve the oxygen level below 3 ppm |

Procedure:

Pemetrexed-containing compositions were prepared by dissolving pemetrexed disodium salt to a concentration of 10 mg/ml in water. Monothioglycerol, sodium citrate tribasic, benzyl alcohol and sodium chloride were added to the solution. The pH was adjusted to 6 to 9.5 with 0.1N sodium hydroxide or 0.1 N hydrochloric acid. The obtained sterile solution is then filled in vials, sealed, labelled and were maintained at 40° C. and 25° C. and analyzed for drug content and impurity profile.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to a "cosolvent" refers to a single cosolvent or to combinations of two or more cosolvents, and the like.

We claim:

1. A long term storage multi-dose ready-to-dilute or ready-to-use pharmaceutical liquid formulation comprising: a) pemetrexed or a pharmaceutically acceptable salt thereof; b) an antioxidant; c) a preservative; d) a buffering agent; and e) a pharmaceutically acceptable fluid, wherein the formulation when stored for six months in a sealed, sterile vial at 25° C./60% RH and 40° C./75% RH contains no more than 1.0% total impurity as measured by HPLC, wherein the preservative comprises benzyl alcohol in an amount from about 3 mg/mL to about 25 mg/mL of the formulation.

2. The pharmaceutical formulation according to claim 1 wherein the antioxidant is selected from the group comprising: monothioglycerol, L-cysteine and thioglycolic acid, acetyl cysteine, butylated hydroxy toluene, butylated hydroxy anisole, DL-tocopherol, sodium metabisulfite, sodium formaldehyde sulfoxylate, EDTA and its derivatives, methionine, ascorbic acid, citric acid and its pharmaceutically acceptable salts, sodium sulfite and its derivative, and combinations thereof.

3. The pharmaceutical formulation according to claim 1 wherein the antioxidant is monothioglycerol.

4. The pharmaceutical formulation according to claim 1 wherein the antioxidant is present in an amount in the range of about 2 mg/mL to about 10 mg/mL or in the range of about 2.5 mg/mL to about 5 mg/mL of the formulation.

5. The pharmaceutical formulation according to claim 1 wherein the preservative is selected from the group of phenylmercuric nitrate, thiomersal, benzalkonium chloride, benzethonium chloride, phenol, cresol, chlorobutanol and combinations thereof.

6. The pharmaceutical formulation according to claim 1 wherein the preservative is m-cresol present in the formulation in an amount from about 0.1 mg/mL to about 3 mg/mL of the formulation.

7. The pharmaceutical formulation according to claim 1 wherein the buffering agent is selected from the group comprising: salts of organic or inorganic acids, bases, amino acids, citrates, phosphates, tartrates, succinates, adipates, maleates, lactates, acetates, bicarbonate, carbonate ions, and combinations thereof.

8. The pharmaceutical formulation according to claim 1 wherein the buffering agent is sodium citrate disodium, sodium citrate tribasic, sodium citrate monobasic or combinations thereof.

9. The pharmaceutical formulation according to claim 1 wherein the buffering agent is present in an amount in the range of about 0.5 mg/mL to 30 mg/mL or about 1 mg/mL to about 20 mg/mL.

10. The pharmaceutical formulation according to claim 1 wherein the pharmaceutically acceptable fluid is selected from the group comprising: aqueous solutions, water, saline, $D_5W$, propylene glycol (PG) and combinations thereof.

11. The pharmaceutical formulation according to claim 1 wherein the pharmaceutically acceptable fluid is water or a mixture of about 10% propylene glycol (PG) and about 90% water.

12. The pharmaceutical formulation according to claim 1 further comprising pharmaceutical acceptable excipients comprising surfactants, isotonicity agents or combinations thereof.

13. The pharmaceutical formulation according to claim 1, wherein the formulation is a ready-to-use formulation, in which the isotonicity agent is 0.9% NaCl.

14. The pharmaceutical formulation according to claim 1 wherein the pH of the formulation is from 6.0 to 9.5 or is about 8.0.

15. The pharmaceutical formulation according to claim 1 which is in a form suitable for parenteral administration.

16. The pharmaceutical formulation according to claim 1 wherein the pemetrexed is the disodium salt thereof.

17. The pharmaceutical formulation according to claim 1 wherein pemetrexed is present in an amount of about 25 mg/mL of the ready-to-dilute formulation.

18. The pharmaceutical formulation according to claim 1 wherein pemetrexed is present in an amount of about 5 mg/mL of the ready-to-use formulation.

19. A long term storage multi-dose ready-to-dilute or ready-to-use pharmaceutical liquid formulation comprising: a) pemetrexed or a pharmaceutically acceptable salt thereof; b) an antioxidant; c) a preservative; d) a buffering agent; and e) a pharmaceutically acceptable fluid, and e) wherein the formulation when stored for six months in a sealed, sterile vial at 25° C./60% RH and 40° C./75% RH contains no more than 1.0% total impurity as measured by HPLC, wherein the pharmaceutical formulation further comprising cisplatin, or carboplatin in combination with pembrolizumab.

20. A kit comprising at least one pharmaceutically acceptable vial or container containing one or more doses of the pharmaceutical formulation according to claim 1 along with instructions for storage and use of the kit.

21. A long term storage multi-dose ready-to-dilute or ready-to-use pharmaceutical liquid formulation comprising: a) pemetrexed or a pharmaceutically acceptable salt thereof b) an antioxidant; c) a preservative; d) a buffering agent; and e) a pharmaceutically acceptable fluid, wherein the formulation when stored for six months in a sealed, sterile vial at 25° C./60% RH and 40° C./75% RH contains no more than 1.0% total impurity as measured by HPLC, wherein the preservative comprises m-cresol in an amount from about 0.1 mg/mL to about 3 mg/mL of the formulation.

22. A method of producing a pharmaceutical formulation comprising the steps of:
(a) dissolving pemetrexed or pharmaceutically acceptable salt thereof in a pharmaceutically acceptable fluid to form a solution;
(b) adding an antioxidant, a preservative and a buffering agent to the solution; and
(c) adjusting the pH of the solution to from about 6.0 to about 9.0, wherein the preservative comprises benzyl alcohol in an amount from about 3 mg/mL to about 25 mg/mL of the formulation.

23. A method for treating malignant pleural mesothelioma or non-squamous, non-small cell lung cancer comprising administering a pharmaceutical formulation according to claim 1 to a subject in need thereof.

24. A method according to claim 23 further comprising administrating cisplatin or carboplatin in combination with pembrolizumab.

* * * * *